(12) United States Patent
Elahi et al.

(10) Patent No.: US 7,722,670 B2
(45) Date of Patent: May 25, 2010

(54) ORBITAL IMPLANT DEVICE

(76) Inventors: Ebrahim Elahi, 317 W. 95th St., Apt. 5C, New York, NY (US) 10025; Keivan Razavi, 420 E. 55 St., Apt. 9A, New York, NY (US) 10022

( * ) Notice: Subject to any disclaimer, the term of this patent is extended or adjusted under 35 U.S.C. 154(b) by 882 days.

(21) Appl. No.: 11/438,460

(22) Filed: May 22, 2006

(65) Prior Publication Data
US 2007/0270634 A1  Nov. 22, 2007

(51) Int. Cl.
*A61F 2/14* (2006.01)
*A61F 2/16* (2006.01)
*A61F 2/52* (2006.01)

(52) U.S. Cl. .................. 623/4.1; 623/6.13; 623/6.19; 623/6.38; 623/6.64; 623/7

(58) Field of Classification Search ............. 623/6.13, 623/6.19, 4.1, 294, 6.38, 6.64, 7, 8, 7.8; 604/22
See application file for complete search history.

(56) References Cited

U.S. PATENT DOCUMENTS

| | | | |
|---|---|---|---|
| 5,330,529 A * | 7/1994 | Cepela | 623/6.64 |
| 5,562,731 A | 10/1996 | Cumming | |
| 5,584,880 A | 12/1996 | Martinez | |
| 5,919,233 A | 7/1999 | Knopf et al. | |
| 6,110,202 A | 8/2000 | Barraquer et al. | |
| 6,171,337 B1 | 1/2001 | Galin | |
| 6,520,989 B1 * | 2/2003 | Eaton | 623/7 |
| 6,969,405 B2 * | 11/2005 | Suddaby | 623/17.12 |
| 7,160,931 B2 * | 1/2007 | Cheng et al. | 523/113 |
| 2004/0029994 A1 * | 2/2004 | Cheng et al. | 523/113 |
| 2004/0039445 A1 * | 2/2004 | Grip | 623/4.1 |
| 2007/0112318 A1 * | 5/2007 | Leahy et al. | 604/294 |
| 2008/0221679 A1 * | 9/2008 | Hamas | 623/8 |
| 2009/0043385 A1 * | 2/2009 | Hamilton | 623/8 |

OTHER PUBLICATIONS

P.C. Leung et al.; Biodegradable Thermosensitive Implant for Approximating Cylindrical Structures: A Preliminary Study; Microsurgery 23:123-129, 2003 Wiley-Liss, Inc.
Bret Ballou et al.; Thermal-responsive Poly(N-isopropylacrylamide) for use in tissue scaffolding, controlled drug-delivery and protein concentrators; Sep. 26, 2005; www.chemweb.calpoly.edu/chem./hagen/446/Webproject.htm.

* cited by examiner

*Primary Examiner*—Paul B Prebilic
*Assistant Examiner*—Jacqueline Woznicki

(57) ABSTRACT

According to an embodiment of the present invention, an implant device may be provided. The implant may be adapted to manipulate the position of an eyeball associated with a patient, whereby the device comprises an insertion device including a first and a second portion. The first portion may include a first thickness and may be adapted to elevate the position of the eyeball. The second portion may include a second thickness and/or a second position relative the first portion for moving the position of the eyeball in a forward direction.

10 Claims, 13 Drawing Sheets

ORBITAL IMPLANT DEVICE

COPYRIGHT AND LEGAL NOTICES

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyrights whatsoever.

BACKGROUND OF THE INVENTION

The present invention relates generally to a device for repositioning the eyeball, and more particularly to an implant device for repositioning the eyeball such that, among other things, an improved cosmetic appearance associated with the patient's facial characteristics may be created.

SUMMARY OF THE INVENTION

According to an embodiment of the present invention, an orbital implant device may be provided. The implant device may be adapted to manipulate the position of an eyeball associated with a patient, whereby the implant device may comprise an insertion device including a first and a second portion. The first portion may include a first thickness and may be adapted to elevate the position of the eyeball. The second portion may include a second thickness and may be adapted to move the position of the eyeball in a forward direction. The thickness variation of the first and/or second portion of the implant may also be adapted to provide a multi-dimensional adjustment of the position of the eyeball.

According to an embodiment of the present invention, an implant device may be provided. The implant device may be adapted to manipulate the position of an eyeball associated with a patient, whereby the implant device may comprise an insertion device including a first and a second portion. The first portion may include a first thickness and may be adapted to elevate the position of the eyeball to a first position (e.g., lifting the eyeball). The second portion may be manipulated to a second position relative to the first position for moving the position of the eyeball in a forward direction (e.g., towards the front of the eye socket).

According to another embodiment of the present invention, the insertion device may comprise an intake mechanism for controlling the first thickness, whereby controlling the first thickness is associated with elevating the position of the eyeball.

According to another embodiment of the present invention, the insertion device may comprise an intake mechanism for controlling the second thickness, whereby controlling the second thickness is associated with moving the eyeball in the forward direction.

According to another embodiment of the present invention, the first portion and second portion may comprise an obtuse angle.

According to another embodiment of the present invention, the insertion device may comprise an intake mechanism for controlling the first and second thickness, whereby controlling the first and second thickness is associated with elevating the position of the eyeball and moving the eyeball in the forward direction, respectively.

According to another embodiment of the present invention, the intake mechanism may comprise a valve device.

According to another embodiment of the present invention, the insertion device may comprise a poly(N-isopropylacrylamide) material, wherein the controlled application of an aqueous fluid to the poly(N-isopropylacrylamide) material of the first portion is associated with manipulating the first thickness.

According to another embodiment of the present invention, the insertion device may comprise a poly(N-isopropylacrylamide) material, wherein the application of an aqueous fluid to the poly(N-isopropylacrylamide) material of the second portion is associated with manipulating the second thickness.

According to another embodiment of the present invention, the insertion device may comprise a poly(N-isopropylacrylamide) material, wherein the application of an aqueous fluid to the poly(N-isopropylacrylamide) material of both the first and the second portion is associated with manipulating the first and the second thickness, respectively.

According to another embodiment of the present invention, the obtuse angle may comprise a range of about 145-160 degrees.

According to another embodiment of the present invention, a method of administering an implant device to an eyeball within an orbit is provided, wherein the orbit may include an orbit floor and a periosteum covering the orbit floor. The method may comprise incising the periosteum at a location substantially near a rim of the orbit and elevating the periosteum away from the orbit floor based on the incision. The implant may then be placed between the orbit floor and elevated periosteum, such the that implant is positioned on the orbit floor. A dimension associated with the implant may be manipulated, whereby the manipulated dimension repositions the position of the eyeball.

According to another embodiment of the present invention, manipulating the dimension may comprise manipulating a thickness associated with the orbital implant.

According to another embodiment of the present invention, manipulating the thickness may comprise delivering a material into the orbital implant.

According to another embodiment of the present invention, the material may comprise a fluid.

According to another embodiment of the present invention, the fluid may comprise a gel.

According to another embodiment of the present invention, delivering the material may comprise providing an intake mechanism (e.g., a valve mechanism) for injecting the material into the orbital device.

According to another embodiment of the present invention, a method is provided for repositioning a eyeball within an orbit. The method may comprise implanting an implant device with respect to a floor of the orbit and manipulating a first thickness associated with a first portion of the implant device, wherein the first thickness provides a first repositioning of the eyeball. A second thickness associated with a second portion of the implant device may be manipulated, wherein the second thickness provides a second repositioning of the eyeball.

According to another embodiment of the present invention, the first and second thickness may be substantially equal.

According to another embodiment of the present invention, the first repositioning may comprise an upward movement of the eyeball and the second repositioning comprises a forward movement of the eyeball.

According to another embodiment of the present invention, the forward and upward movement of the eyeball may compensate for a loss of orbital fat within the orbit.

According to another embodiment of the present invention, an implant device is adapted to manipulate the position of an eyeball associated with a patient. The device may comprise an insertion device, where the insertion device includes a substantially planer portion that includes a first thickness. The first thickness is adapted to elevate the position of the eyeball from a first position to a second position based on the planer portion being adapted to include a second thickness.

According to another embodiment of the present invention, the first and the second position may comprise a positional change associated with the eyeball along the inferior-superior direction relative to an orbit of the eyeball.

According to another embodiment of the present invention, an implant device is adapted to manipulate the position of an eyeball associated with a patient. The device may comprise an insertion device, where the insertion device includes a first portion and a second portion. The second portion may be manipulated relative to the first portion between a first position and a second position and may be adapted to provide a forward positioning of the eyeball at the second position.

According to another embodiment of the present invention, the first and second position may comprise a positional change associated with the eyeball along the anterior-posterior direction relative to an orbit of the eyeball.

According to another embodiment of the present invention, an implant device is adapted to provide position manipulation of an eyeball associated with a patient. The device may comprise a plurality of insertion devices, where the insertion devices each include a substantially planer portion including a first thickness. The position of the eyeball may be elevated from a first position to a second position based on stacking at least two of the insertion devices on top of each other.

According to another embodiment of the present invention, the first thickness may vary between insertion devices, such that a designated elevation of the eyeball from the first to the second position may be accomplished selectively by selecting insertion devices of different thicknesses.

According to another embodiment of the invention, an implant device associated with repositioning an eyeball within an eye socket, and located under the eyeball may comprise an elongate body that includes a partial circular shape having an open end and a circular portion. The open end may be positioned at the front of the eye socket and the circular portion may be positioned at the rear of the eye socket. The elongate body includes a first cross section adapted to be manipulated to a second cross section for providing an upward repositioning of the eyeball.

According to another embodiment of the invention, the circular portion comprises a region adapted to be manipulated such that a forward repositioning of the eyeball is provided based on the region expanding in direction toward the front of the eye socket.

According to another embodiment of the invention, an implant device associated with repositioning an eyeball within an eye socket, and located under the eyeball may comprise an elongate body that includes a partial circular shape having an open end and a circular portion. The open end may be positioned at the rear of the eye socket and the circular portion may be positioned at the front of the eye socket. The elongate body includes a first cross section adapted to be manipulated to a second cross section for providing an upward repositioning of the eyeball.

According to another embodiment of the invention, the elongate body comprises a plurality of regions located adjacent the open end and adapted to be manipulated such that a forward repositioning of the eyeball is provided based on the plurality of regions expanding in direction toward the front of the eye socket.

BRIEF DESCRIPTION OF DRAWINGS

The invention is illustrated in the figures of the accompanying drawings, which are meant to be exemplary and not limiting, and in which like references are intended to refer to like or corresponding parts, in which:

FIGS. 13A-14C are cross sectional views of orbital implants according to yet another embodiment of the present invention.

DETAILED DESCRIPTION

Figure 1:
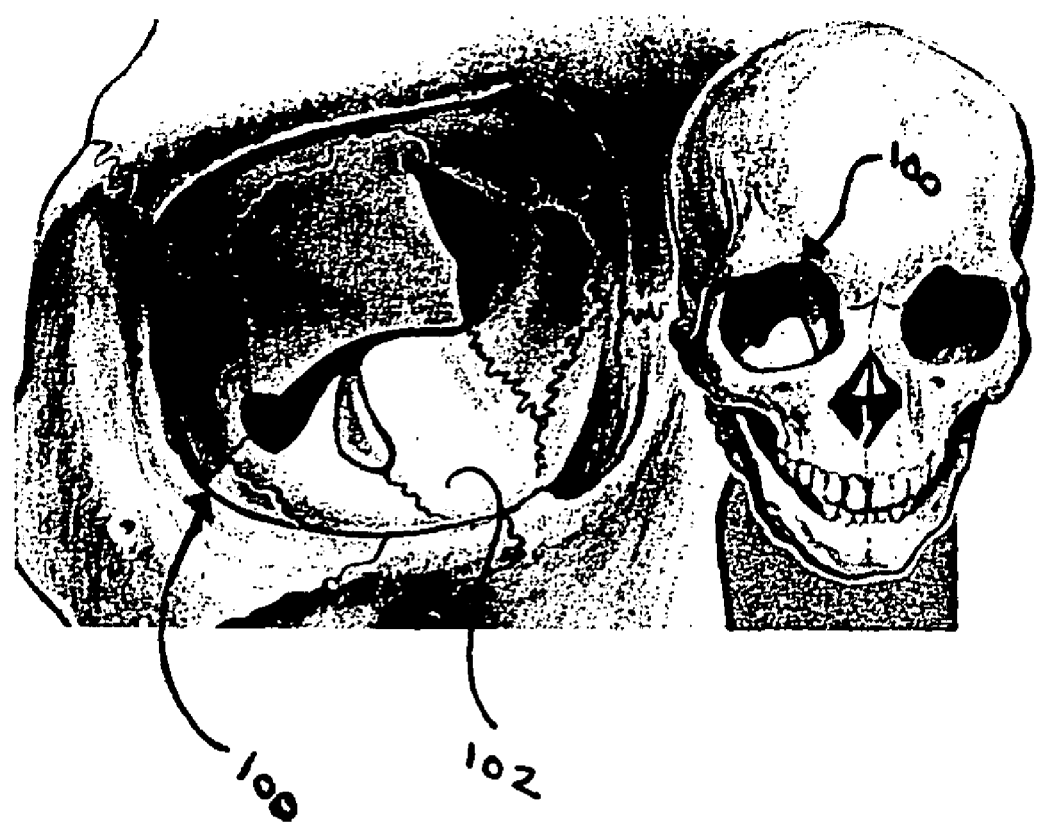
FIG. 1 is an orbit of a human eye according to an embodiment of the present invention.

FIG. 1 illustrates an orbit 100 of a human eye according to an embodiment of the present invention. An eyeball 200 (FIG. 2) comprises approximately six cubic centimeters of volume and is suspended within an orbit 100 of around thirty five cubic centimeters by, among other anatomical parts, orbital fat 202 and muscles such as, for example, inferior rectus muscle 204 and interior oblique muscle 206 etc.

Figure 2:
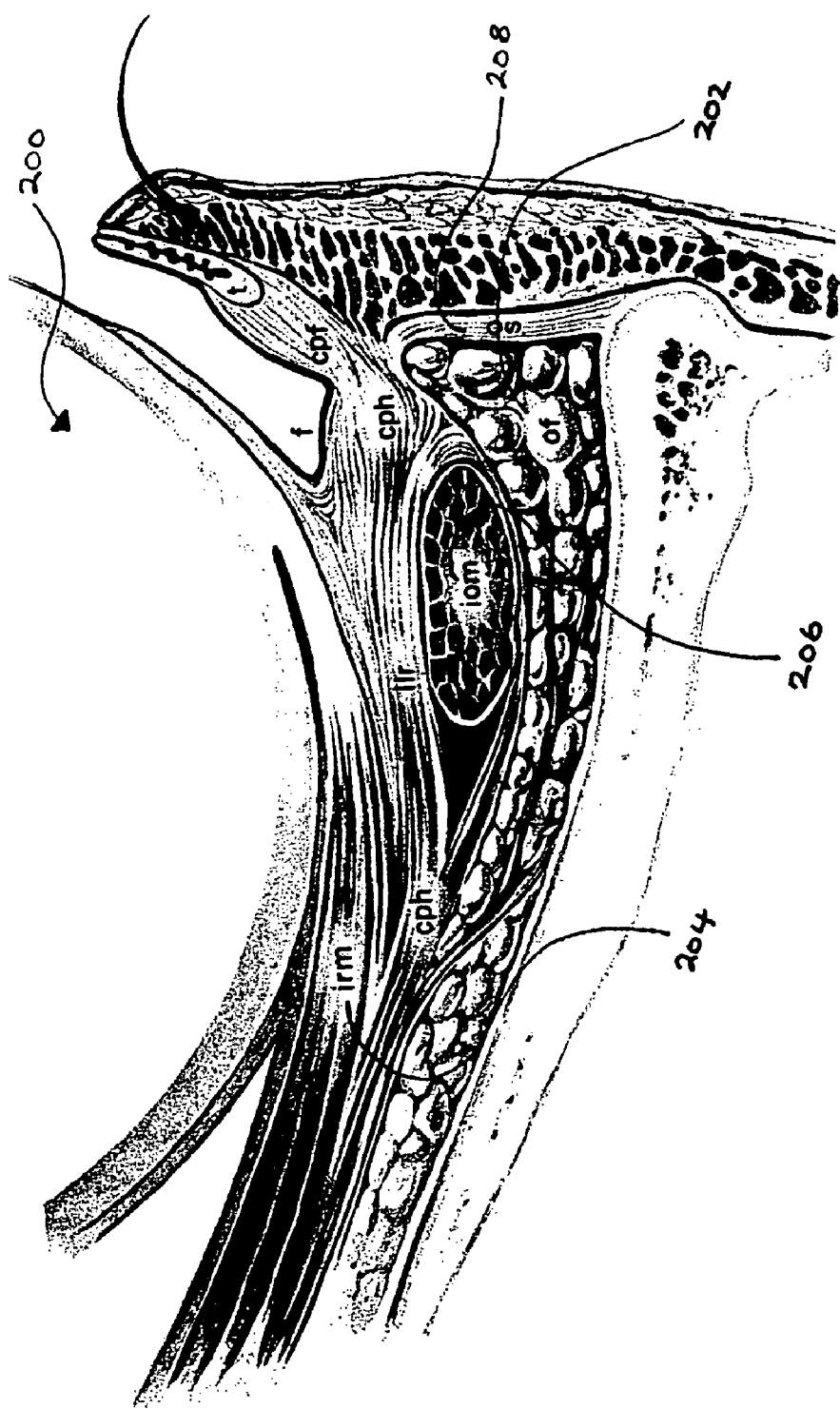
FIG. 2 is a partial cross section of a human eye according to an embodiment of the present invention.

FIG. 2 is a partial cross section of a human eye according to an embodiment of the present invention. Medical conditions such as superior sulcus deformity and/or enophthalamos/hypoglobus may, among other symptoms, cause the eyeball 200 to sink within orbit 100 (FIG. 1). This may lead to a less desirable cosmetic appearance associated with the eye, which may visually enhance the appearance of aging in a subject. One of the causes of this visual appearance is the loss of orbital fat in the eye, which may be caused naturally through the aging process, or artificially through cosmetic surgery. For example, surgery for removing bags under a subject's eyes may involve removing orbital fat 202 that has been pushed forward towards the front of the eye stretching the orbital septum 208. However, once the orbital fat of the eye 200 is removed, it cannot be naturally replaced. Thus, the visual effect of this orbital fat 202 loss (e.g., surgery, aging, etc.) may include a repositioning (i.e., downward displacement) of the eyeball 200 within orbit 100 (FIG. 1).

Figure 3A:
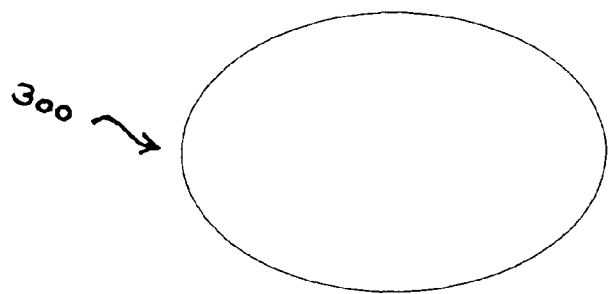
FIGS. 3A-3C are top and side views of an orbital implant according to embodiment of the present invention.
Figure 3B:
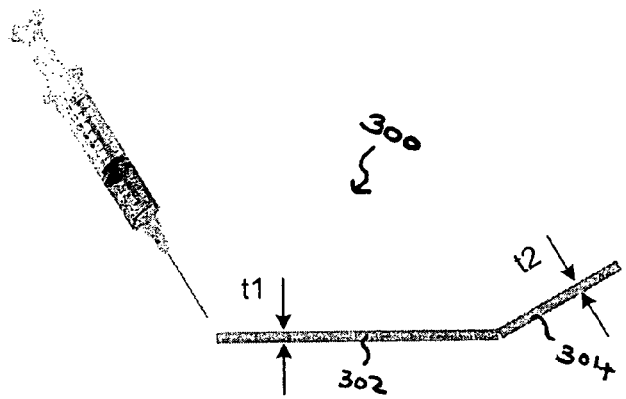
Figure 3C:
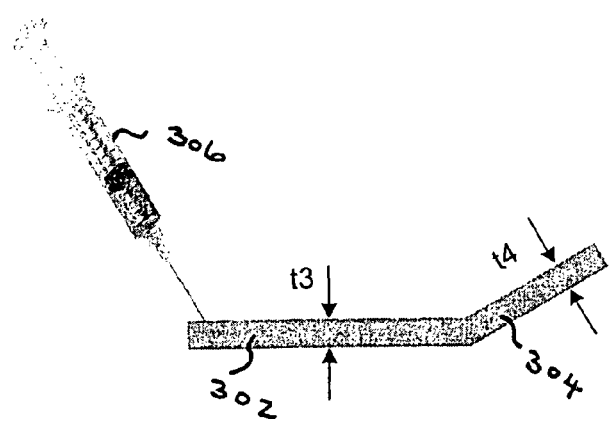

FIGS. 3A-3C illustrate a top view and cross sectional side views, respectively, of an insertion device such as an implant device for positioning the eyeball 200 (FIG. 2) within orbit 100 (FIG. 1) according to an embodiment of the present invention. FIG. 3A illustrates a top view of implant 300, where the shape of the implant is adapted to fit within the dimensions of the floor 102 (FIG. 1) of orbit 100 (FIG. 1). The implant 300 may be positioned bellow the eyeball for providing any necessary positional adjustments.

FIG. 3B is a cross sectional side view of implant 300. As illustrated, implant 300 may comprise a first section 302 including a thickness t1 and a second section 304 having a thickness t2. Sections 302 and 304 have an angular relationship, such that an obtuse angle (Δ) may be formed between the sections 302, 304. The obtuse angle between sections 302 and 304 may be in the range of 145-160 degrees. It may be appreciated that this angular range may differ based on the magnitude of eyeball repositioning needed. By adjusting thickness t1 of section 302, the height position of the eyeball may be manipulated. By manipulating the angle Δ between section 302 and 304, the forward position of the eyeball may be manipulated. Similarly, by adjusting thickness t2 of section 304, a forward positioning of the eyeball may be provided. It may also be possible to vary both angle Δ and thickness t2 in order to manipulate the forward positioning of the eyeball. For example, section 302 may include a length of approximately 10-12 millimeters and section 304 may include a length of approximately 8-12 millimeters. The width of implant 300 may also be in the region of 12 millimeters.

FIG. 3C illustrates the cross sectional side view of implant 300 following the adjustment of thicknesses t1 and t2 (FIG. 3B). A delivery mechanism such as a syringe 306 may be used for controllably adjusting regions 302 and 304 to thicknesses t3 and t4, respectively. The delivery mechanism and the solution (i.e., gel, liquid, etc.) that is injected, delivered, or applied to implant 300 may depend on the material and construction of the implant 300. For example, the delivery mechanism may include only a syringe 306. Alternatively, the delivery mechanism may include a valve mechanism (not shown) associated with the implant that controls the inward and outward flow of the solution within the implant 300. The delivery mechanism may further comprise a device (not shown) for injecting the solution via the valve mechanism into the implant 300, whereby the injecting device may include, but is not limited to, a syringe like device.

For example, implant 300 may comprise a sack construction that may be filled with a saline or other solution for adjusting the thickness of implant 300. Alternatively another liquid of gel may be used to fill the contents of the sack construction. The liquid or gel should be of a chemical composition that is safe for use in and about the eye, since any damage or malfunctioning of the implant 300 may cause the gel or liquid to ooze out of the implant 300 and come in direct contact with the eye. Implant 300 may also comprise a sack construction that may be filled with air in order to establish the required thickness of sections 302 and 304. It may also be possible to design the implant 300, such that its liquid or gel content gradually seep out of the implant 300 in order to automatically deliver a particular medicated solution to the eye or orbit. In such an exemplary embodiment, the implant 300 may serve both as a medical or drug delivery device, and as a means for repositioning the eyeball. The implant may include a dedicated region (not shown) that is filled with medication for the purpose of delivery to the eye or orbit following the positioning of the implant within the eye (e.g., see FIG. 7).

After a finite period of time, it may be necessary for the doctor or surgeon (e.g., ophthalmologist or oculoplastic surgeon) to refill (e.g., through a valve mechanism) the contents of the implant 300 in order to reposition the eyeball, where the refill may be medicated or non-medicated. Once refilled, it may also be possible, through a delivery mechanism (e.g., miniature valve, syringe, etc.), to ensure that the implant's 300 contents does not more readily seep out of the implant and into the eye. Once implant 300 is filled with a gel or liquid solution (e.g., by means of a syringe), the opening through which the gel or liquid was delivered may be sealed using, for example, an adhesive material. The opening may also be sealed using a multitude of other techniques. In other alternative exemplary embodiments, different valve mechanisms (not shown) may be utilized to control the flow of gel or liquid into and out of implant 300.

For example, implant 300 may comprise a poly(N-isopropylacrylamide) material or other gel-type composition that provides a controllable volume change (e.g., expansion ratio) based on the absorption of a liquid such as, for example, water. For example, by controllably applying the liquid (e.g., water) to the poly(N-isopropylacrylamide) material, thicknesses t1 and t2 (FIG. 3B) may be adjusted to thicknesses t3 and t4 (FIG. 3C), respectively. Such gel-type materials for use in implant 300 may be manufactured by POLY-GEL L.L.C., based in Whippany, N.J.

Figure 4A:
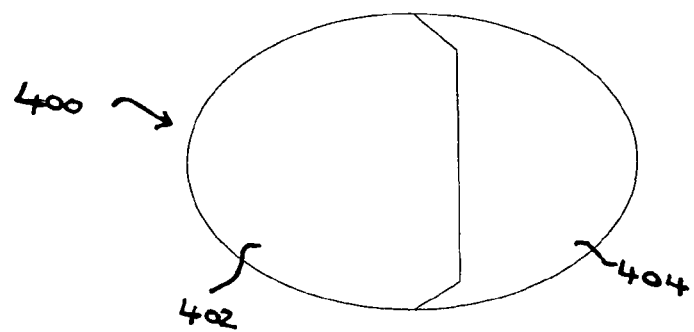
FIGS. 4A-4C are top and side views of an orbital implant according to another embodiment of the present invention.
Figure 4B:
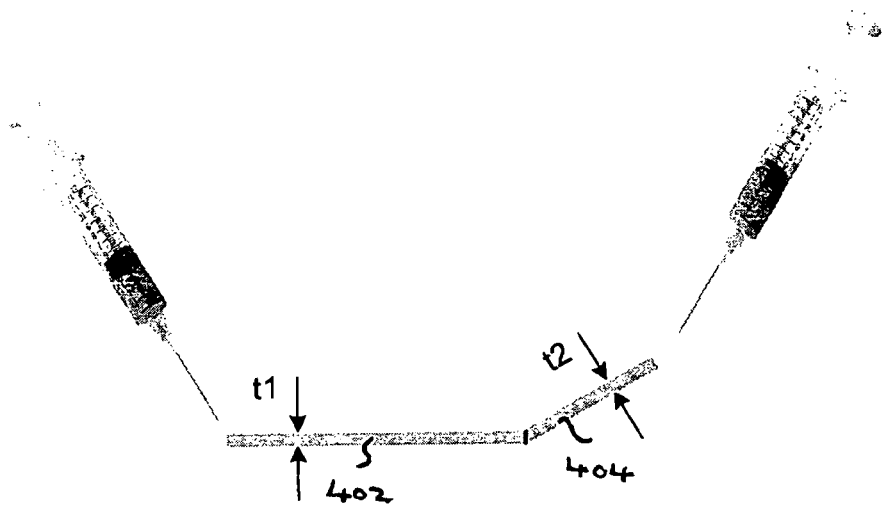
Figure 4C:
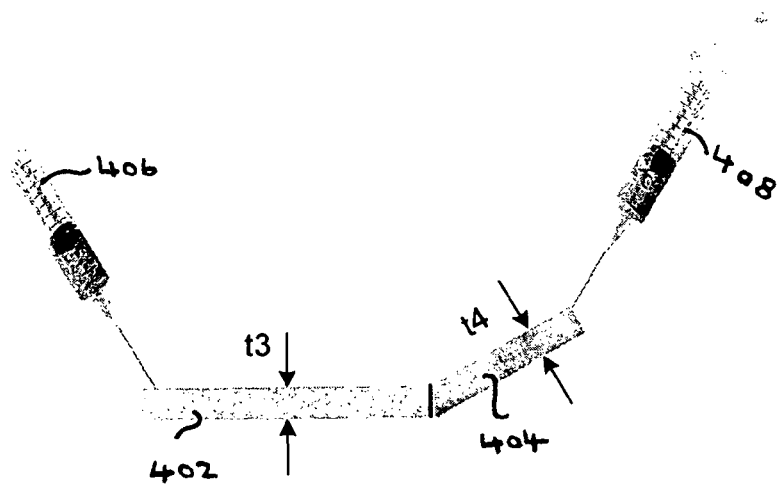

FIGS. 4A-4C illustrate a top view and cross sectional side views, respectively, of an insertion device such as an implant device for positioning the eyeball 200 (FIG. 2) within orbit 100 (FIG. 1) according to another embodiment of the present invention. FIG. 4A illustrates a top view of implant 400, where the shape of the implant is adapted to fit within the dimensions of the floor 102 (FIG. 1) of orbit 100 (FIG. 1). The implant 400 may be positioned bellow the eyeball for providing any necessary positional adjustments.

FIG. 4B is a cross sectional side view of implant 400. As illustrated, implant 400 may comprise a first section 302 including a thickness t1 and a second section 304 having a thickness t2. Sections 402 and 404 have an angular relationship, such that an obtuse angle (Δ) may be formed between the sections 402, 404. The obtuse angle between sections 402 and 404 may be in the range of 145-160 degrees. It may be appreciated that this angular range may differ based on the magnitude of eyeball repositioning needed. By adjusting thickness t1 of section 402, the height position of the eyeball may be manipulated. By manipulating the angle Δ between section 402 and 404, the forward position of the eyeball may be manipulated. Similarly, by adjusting thickness t2 of section 404, a forward positioning of the eyeball may be provided. It may also be possible to vary both angle Δ and thickness t2 in order to manipulate the forward positioning of the eyeball. Referring to FIG. 4A, sections 402 and 404 are separate regions that may include separately controllable thicknesses. For example, section 402 may include a length of approximately 10-12 millimeters and section 404 may include a length of approximately 8-12 millimeters. The width of implant 400 may also be in the region of 12 millimeters.

FIG. 4C illustrates the cross sectional side view of implant 400 following the adjustment of thicknesses t1 and t2 (FIG. 4B). Delivery mechanisms such as syringes 406 and 408 may be used for controllably adjusting sections 402 and 404 to thicknesses t3 and t4, respectively. The delivery mechanism and the solution that is injected, delivered, or applied to implant 400 may depend on the material and construction of the implant 400, as previously explained. For example, the delivery mechanism may include one or more syringes such as, for example, syringes 406 and 408. Alternatively, the delivery mechanism may include a valve mechanism (not shown) associated with the implant that controls the inward and outward flow of the solution within each of sections 402 and 404 of implant 400. The delivery mechanism may further comprise a device (not shown) for injecting the solution via one or more valve mechanisms into the implant 400, whereby the injecting device may include, but is not limited to, a syringe like device.

Thickness t1 associated with section 402 may be varied to thickness t3 without affecting the thickness of section 404. Similarly, thickness t2 associated with region 404 may be varied without affecting the thickness of section 402. Thus, the height positioning and forward positioning of eyeball 200 (FIG. 2) may be achieved independently via sections 402 and 404, respectively.

For example, implant 400 may also comprise a sack construction that may be filled with a saline or other solution for adjusting the thickness of implant 300. Alternatively another liquid of gel may be used to fill the contents of the sack construction. The liquid or gel should be of a chemical composition that is safe for use in and about the eye, since any damage or malfunctioning of the implant 400 may cause the gel or liquid to ooze out of the implant 400 and come in direct contact with the eye. Implant 400 may also comprise a sack construction that may be filled with air in order to establish the required thickness of sections 402 and 404. It may also be possible to design the implant 400, such that its liquid or gel content gradually seep out of the implant 400 in order to automatically deliver a particular medicated solution to the eye. In such an exemplary embodiment, the implant 400 may serve both as a medical or drug delivery device, and as a means for repositioning the eyeball.

After a finite period of time, it may be necessary for the doctor or surgeon (e.g., opthalmologist) to refill the contents of the implant 400 in order to reposition the eyeball, where the refill may be medicated or non-medicated. Once refilled, it may also be possible, through a delivery mechanism (e.g., miniature valve, syringe, etc.), to ensure that the implant's 400 contents does not more readily seep out of the implant and into the eye. Once implant 400 is filled with a gel or liquid solution (e.g., by means of a syringe), the opening through which the gel or liquid was delivered may be sealed using, for example, an adhesive device. The opening may also be sealed using a multitude of other techniques. In other embodiment, different valve mechanisms (not shown) may be utilized to control the flow of gel or liquid into and out of implant 400.

Implant 400 may also, for example, comprise a poly(N-isopropylacrylamide) material or other gel-type composition that provides a controllable volume change (e.g., expansion ratio) based on the absorption of a liquid such as, for example, water. For example, by controllably applying the liquid (e.g., water) to the poly(N-isopropylacrylamide) material, thicknesses t1 and t2 (FIG. 3B) may be adjusted to thicknesses t3 and t4 (FIG. 3C), respectively. Such gel-type materials for use in implant 400 may be manufactured by POLY-GEL L.L.C., based in Whippany, N.J.

Figure 5A:
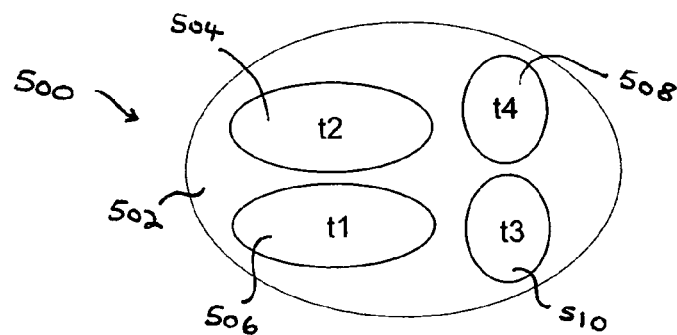
FIGS. 5A-5C are top and side views of an orbital implant according to yet another embodiment of the present invention.
Figure 5B:
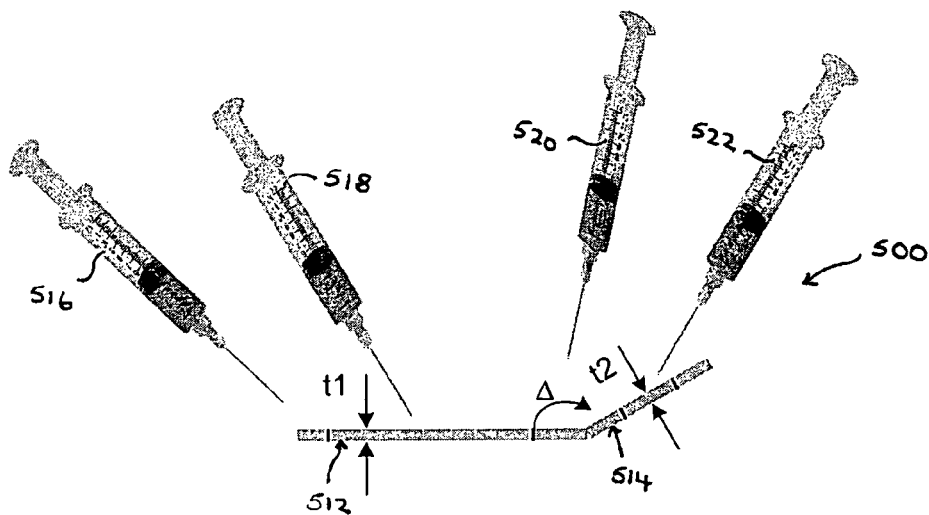
Figure 5C:
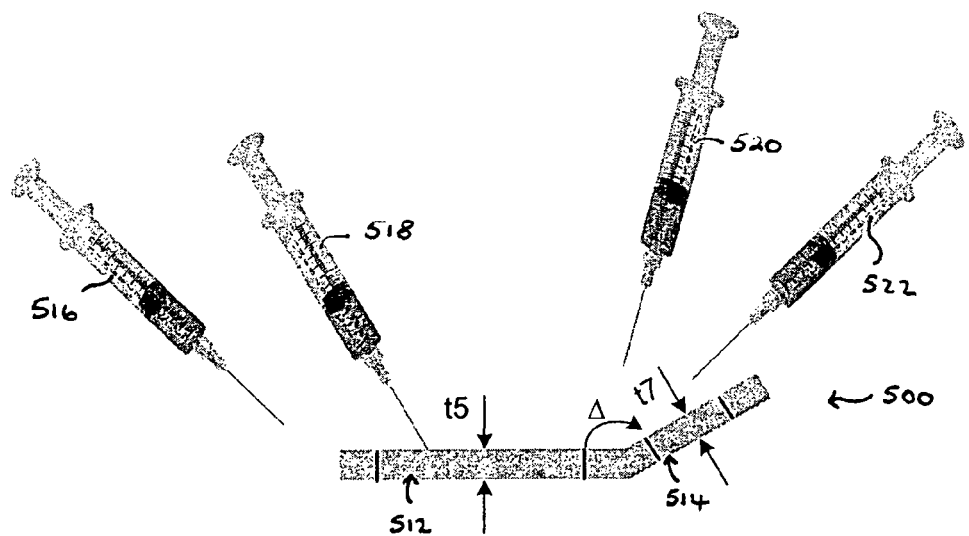

FIGS. 5A-5C illustrate a top view and cross sectional side views, respectively, of an insertion device such as an implant device for positioning the eyeball 200 (FIG. 2) within orbit 100 (FIG. 1) according to another embodiment of the present invention. FIG. 5A illustrates a top view of implant 500, where the shape of the implant is adapted to fit within the dimensions of the floor 102 (FIG. 1) of orbit 100 (FIG. 1). The implant 500 may be positioned bellow the eyeball for providing any necessary positional adjustments. Implant 500 may comprise a substrate region 402 and implant regions 504-510. The thickness of each of implant regions 504-510 may be independently adjusted in order to position eyeball 200 (FIG. 200).

FIG. 5B is a cross sectional side view of implant 500. As illustrated, implant 500 may comprise a first section 512 that includes implant regions 504 (FIG. 1) and 506 FIG. 1), where implant region 504 comprises thickness t1 and implant region 506 comprises thickness t2. Thicknesses t1 and t2 may be independently adjusted. Implant 500 may also comprise a second section 514 that includes implant regions 508 (FIG. 1) and 510 FIG. 1), where implant region 508 comprises thickness t3 and implant region 510 comprises thickness t4. Thicknesses t3 and t4 may also be independently adjusted. Sections 512 and 514 have an angular relationship, such that an obtuse angle ($\Delta$) may be formed between the sections 512, 514. The obtuse angle between sections 512 and 514 may be in the range of 145-160 degrees. It may be appreciated that this angular range may differ based on the magnitude of eyeball repositioning needed. By adjusting thicknesses t1 and t2 of implant regions 504 and 506, respectively, the height position of the eyeball may be manipulated. By manipulating the angle $\Delta$ between section 512 and 514, the forward position of the eyeball may be manipulated. Similarly, by adjusting thicknesses t3 and t4 of implant regions 508 and 510, respectively, a forward positioning of the eyeball may be provided. It may also be possible to vary both angle $\Delta$ and thickness t3 and t4 in order to manipulate the forward positioning of the eyeball. Referring to FIG. 5A, implant regions 504-510 are separate implant regions that may include separately controllable thicknesses and, thus, positioning capabilities associated with an eyeball. For example, section 512 may include a length of approximately 10-12 millimeters and section 514 may include a length of approximately 8-12 millimeters. The width of implant 500 may also be in the region of 12 millimeters.

FIG. 5C illustrates the cross sectional side view of implant 500 following the adjustment of thicknesses t1-t4 (FIGS. 5B and 5C). Delivery mechanisms such as syringes 516-522 may be used for controllably adjusting implant regions 504-510 to thicknesses t5-t8, respectively. The delivery mechanism and the solution that is injected, delivered, or applied to implant 500 may depend on the material and construction of the implant 500, as previously explained. For example, the delivery mechanism may include one or more syringes such as, for example, syringes 516-522. Alternatively, the delivery mechanism may include a valve mechanism (not shown) associated with each of the implant regions, each valve controlling the inward and outward flow of the solution within each of implant regions 504-510 of implant 500. The delivery mechanism may further comprise a device (not shown) for injecting the solution via one or more valve mechanisms into the implant 500, whereby the injecting device may include, but is not limited to, a syringe like device.

For example, implant 500 may also comprise a sack construction, where each of the implant regions 504-510 may be filled with a saline or other solution for adjusting the thicknesses (i.e., t1-t4) associated with implant 500. Alternatively another liquid of gel may be used to fill the contents of the sack construction. The liquid or gel should be of a chemical composition that is safe for use in and about the eye, since any damage or malfunctioning of the implant 500 may cause the gel or liquid to ooze out of the implant 500 and come in direct contact with the eye. Implant 500 may also comprise a sack construction that may be filled with air in order to establish the required thickness of implant regions 504-510. It may also be possible to design the implant 500, such that its liquid or gel content gradually seep out of the implant 500 in order to automatically deliver a particular medicated solution to the eye. In such an exemplary embodiment, the implant 500 may serve both as a medical or drug delivery device, and as a means for repositioning the eyeball.

After a finite period of time, it may be necessary for the doctor or surgeon (e.g., opthalmologist) to refill the contents of the implant 500 in order to reposition the eyeball, where the refill may be medicated or non-medicated. Once refilled, it may also be possible, through a delivery mechanism (e.g., miniature valve, syringe, etc.), to ensure that the implant's 500 contents does not more readily seep out of the implant and into the eye. Once implant 500 is filled with a gel or liquid solution (e.g., by means of a syringe), the opening through which the gel or liquid was delivered may be sealed using, for example, an adhesive device. The opening may also be sealed using a multitude of other techniques. In other embodiment, different valve mechanisms (not shown) may be utilized to control the flow of gel or liquid into and out of the implant regions 504-510 associated with implant 500.

Implant 500 may also, for example, comprise a poly(N-isopropylacrylamide) material or other gel-type composition that provides a controllable volume change (e.g., expansion ratio) based on the absorption of a liquid such as, for example, water. For example, by controllably applying the liquid (e.g., water) to the poly(N-isopropylacrylamide) material, thicknesses $t_1$-$t_4$ (FIG. 3B) may be adjusted to thicknesses $t_5$-$t_8$ (FIG. 3C), respectively. Such gel-type materials for use in implant 500 may be manufactured by POLY-GEL L.L.C., based in Whippany, N.J.

Referring to FIGS. 5A-5C, thickness $t_1$ associated with implant region 504 may be varied to thickness $t_5$, thickness $t_2$ associated with implant region 506 may be varied to thickness $t_6$, thickness $t_3$ associated with implant region 508 may be varied to thickness $t_7$, and thickness $t_5$ associated with implant region 510 may be varied to thickness $t_8$. Thus, the height positioning and forward positioning of eyeball 200 (FIG. 2) may be achieved independently via implant regions 504-510. Referring to FIG. 5A, for example, by increasing the thickness ($t_1$) of implant region 506 relative to the thickness ($t_2$) of implant region 504 a lateral movement of the eyeball (e.g., along the direction of an imaginary axis passing through a patient's temple) may also be possible. Similarly, for example, by decreasing the thickness ($t_1$) of implant region 506 relative to the thickness ($t_2$) of implant region 504, a lateral movement of the eyeball (e.g., along the direction of an imaginary axis passing through a patient's temple) may also be achieved.

According to an embodiment of the invention, different methods of controlling the thickness of an implant may be adopted. It may be possible to construct an implant from a material having one or more characteristics that responds to exposure to electromagnetic signals. For example, one or more wavelengths of light may be used in constant or modulated operational modes (e.g., amplitude modulation, frequency modulation, pulse period variation, etc.) modulated for causing a variation in thickness associated with one or more regions of the implant. In such an embodiment, the material associated with the implant's construction may expand in response to exposure to a particular range of infrared wavelengths (e.g., 1300-1500 nanometers), and in proportion to the intensity of the signal (i.e., at a particular wavelength). Selection of such wavelengths, or generally, such signals, may depend on the material used to manufacture the implant and may depend on its effect on the eye itself. Exposing the eye to such signals should include safety considerations that guarantee no damage to sensitive components of the eye, such as the optic nerve, etc. Alternatively, if the wavelength or signal does have the potential to cause damage to certain components of the eye, the signal propagation should be controlled in a manner that allows it to be focused through, for example, a radiation focusing mechanism such as optical lens system.

Figure 6A:
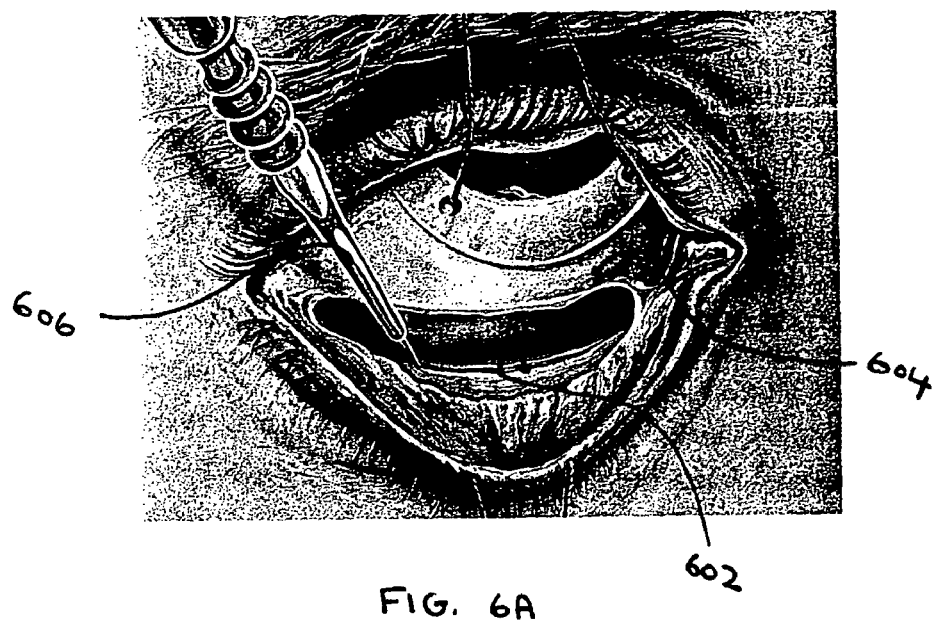
FIGS. 6A and 6B illustrate an incision process for placing an orbital implant in a patient's eye according to an embodiment of the present invention.
Figure 6B:
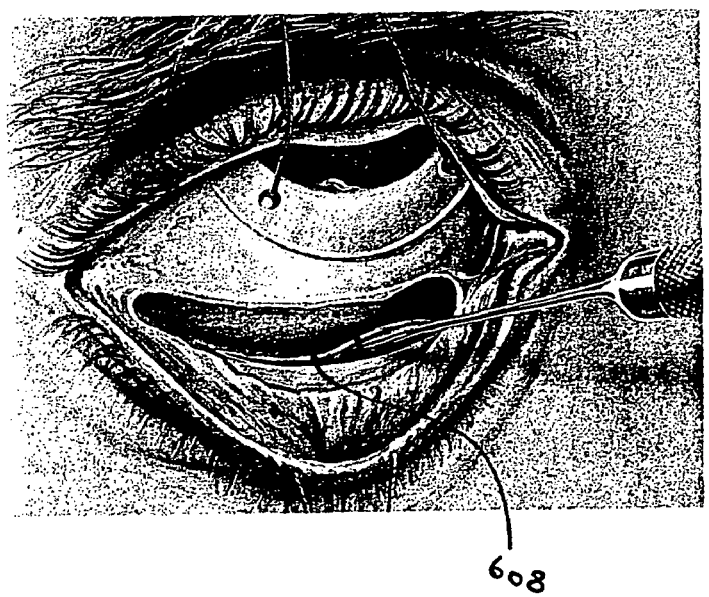

FIGS. 6A and 6B illustrate an incision process for placing an implant in a patient's eye according to an embodiment of the present invention. An implant may be placed under the periosteum layer covering the floor 102 (FIG. 1) or orbit 100 (FIG. 1). Various incision techniques may be available for providing access to the periosteum layer covering floor 102 (FIG. 1). FIGS. 6A and 6B illustrate an inferior conjunctival incision (orbital floor). An incision 602 is made through conjunctiva 604 and down to the rim of the orbit using incision device 606. An incision is then made anterior to the orbital rim through the periosteum. The periosteum may then be elevated, as indicated at 608. Once the incision is made, the implant may be placed between the elevated periosteum and the orbit floor 100 (FIG. 1).

Figure 7A:
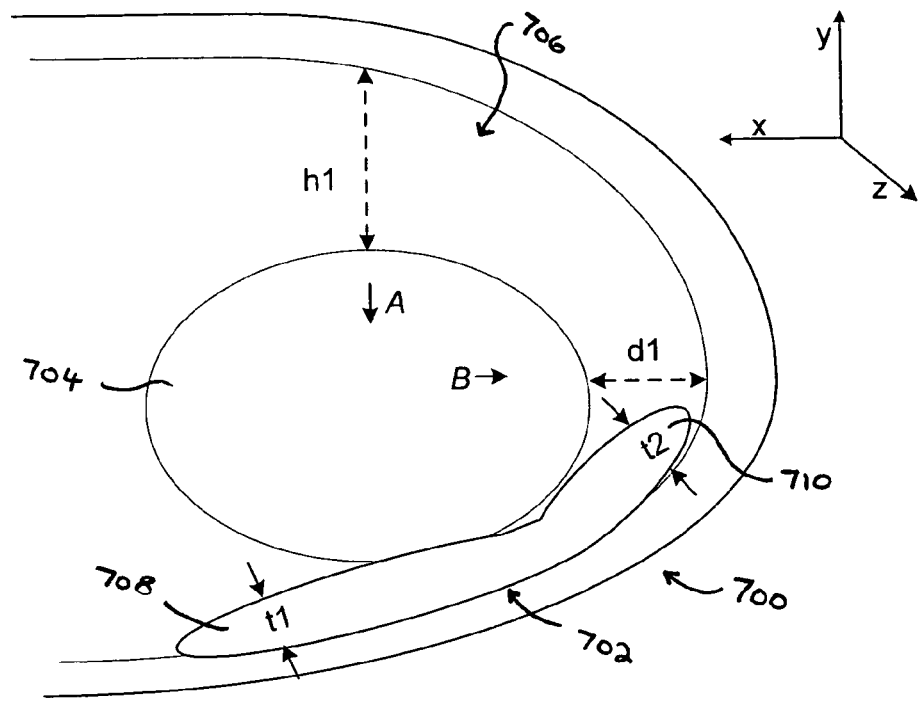
FIGS. 7A and 7B are cross sectional views of an orbital implant within an eye according to an embodiment of the present invention.
Figure 7B:
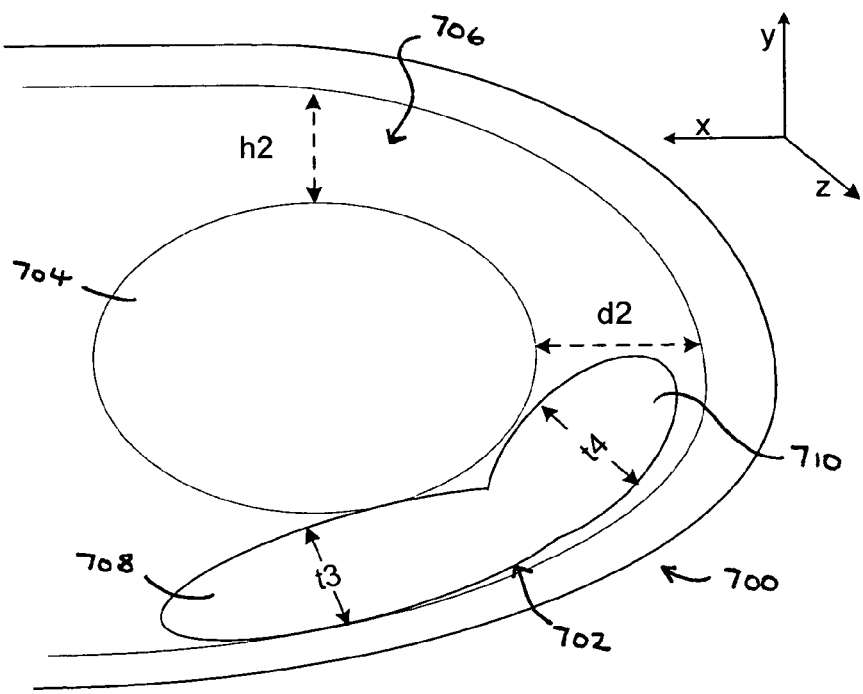

FIGS. 7A and 7B are cross sectional views of an implant placed within an eye 700 according to embodiment of the present invention. As illustrated in FIG. 7A, implant 702 may be placed in the eye using one or more different techniques such as the inferior conjunctival incision method described above. In the case of, for example, a sulcus deformity, eyeball 704 may have sunken within orbit 706. Eyeball 704 may have dropped by a given height (i.e., direction of arrow A) within orbit 706, as well as having moved further back (i.e., direction of arrow B) into orbit 706. Once implant 702 is placed within the eye 700, by manipulating certain characteristics (e.g., thicknesses $t_1$ and $t_2$) associated with implant 702, the shift in position or repositioning of eyeball 704 may be compensated.

As illustrated in FIG. 7B, the repositioning of eyeball 704 may be compensated by, for example, controlling the thickness of sections 708 and 710. Thickness $t_1$ (FIG. 7A) of Section 708 may be increased to thickness $t_3$ (FIG. 7B) in order to increase the vertical position of eyeball 704 from height $h_1$ (FIG. 7A) to height $h_2$ (FIG. 7B). Similarly, thickness $t_2$ (FIG. 7A) of Section 710 may be increased to thickness $t_4$ (FIG. 7B) in order to increase the horizontal position of eyeball 704 from horizontal distance $d_1$ (FIG. 7A) to horizontal distance $d_2$ (FIG. 7B). Thus, by controllably manipulating the thickness of implant 702, position of eyeball 704 may be manipulated. Therefore, in the case of a sulcus deformity condition, it may be possible to control the position of the eyeball in order to restore the eyeball to its original or preferred position, whereby, among other things, an enhanced visual appearance may be accomplished. It may be appreciated that in accordance with the present invention, the implant characteristics (e.g., thickness) may be varied such that the eyeball may be positioned in any three-dimensional direction. For example, referring to implant 500 illustrated in FIGS. 5A-5B, by increasing thickness $t_3$ of region 510 by a greater amount compared to thickness $t_4$ of region 508, the position of an eyeball may be manipulated along direction z (FIGS. 7A and 7B). Thus, any number of implant regions within an implant may be used according to the required magnitude and direction associated with manipulating the position of the eyeball. Also, the exemplary embodiments described herein manipulate the thickness of an implant (e.g., implants 300, 400, 500, and 702) by injecting a solution or gel into a region of the implant. Other techniques may also be used to vary the thickness of one or regions/sections of an implant. For example, based on the material characteristics of the implant, the application of heat may be used to controllably adjust thickness. Alternatively, by using photosensitive materials in the construction of the implant, by applying radiation of a particular wavelength, the thickness of the regions/sections of an implant may be varied.

Each implant may comprise a range of different thicknesses depending on the determined magnitude of eyeball displacement required. For example, an implant may include a maximum un-inflated thickness (e.g., t1 associated with first section 302 of FIG. 3B) of about 1.5 mm (millimeters) and a maximum inflated thickness (e.g., t3 associated with first section 302 of FIG. 3C) of about 15 mm (millimeters).

Figure 8A:
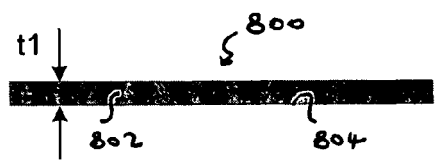
FIGS. 8-10 are cross sectional views of orbital implants according to another embodiment of the present invention.
Figure 8B:
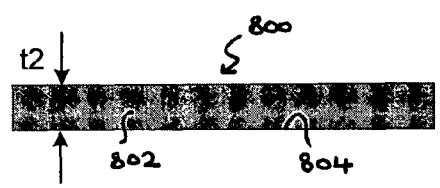

FIGS. 8A and 8B illustrate a cross sectional side view, respectively, of an insertion device such as an implant device for positioning eyeball 200 (FIG. 2) within orbit 100 (FIG. 1) according to an embodiment of the present invention. FIG. 8A is a cross sectional side view of implant 800. As illustrated, implant 800 may comprise a first section 802 including a thickness t1. By adjusting thickness t1 of section 802, the height position of the eyeball may be manipulated. For example, section 802 may include a length of approximately 10-20 millimeters. The width of implant 800 may also be in the region of 12 millimeters.

FIG. 8B illustrates the cross sectional side view of implant 800 following the adjustment of thickness t1 to t2. A delivery mechanism (e.g., a syringe and valve mechanism) may be used for controllably adjusting region 802 from thickness t1 to thicknesses t2. The delivery mechanism and the solution (i.e., gel, liquid, etc.) that is injected, delivered, or applied to implant 800 may depend on the material and construction of the implant 800. For example, the delivery mechanism may include only a syringe (not shown). Alternatively, the delivery mechanism may include a valve mechanism (not shown) associated with the implant that controls the inward and outward flow of a liquid (e.g., saline), gas (e.g., air), or solid (e.g., gel solution) material within implant 800. The delivery mechanism may further comprise a device (not shown) for injecting the material via the valve mechanism into the implant 800, whereby the injecting device may include, but is not limited to, a syringe like device. In another embodiment, implant 800 may have a defined thickness (e.g., thickness t1), whereby a physician (e.g., opthalmologist) may stack several implants such as implant 800 in order to provide a required thickness (e.g., thickness t2 of FIG. 8B) for positioning a patient's eyeball within the orbit. Each of the stacked implants may, for example, have the same thickness. Alternatively, implants having a plurality of different thicknesses may be stacked in order to achieve the required thickness. Bottom surface 804 of implant 800 may be anchored to the floor 102 (FIG. 1) of orbit 100 (FIG. 1) in order to inhibit the movement of the implant 800 and thus the eyeball relative to the orbit 100 (FIG. 1). This may be achieved by providing a bottom surface 804 that comprises tissue integration properties. In such an embodiment, for example, bottom surface 804 may be constructed from bovine, porcine, or cartilage associated with the human anatomy (e.g., nose cartilage). Alternatively, bottom surface 804 of implant 800 may be anchored to the floor 102 (FIG. 1) of orbit 100 (FIG. 1) using a peg, screw, or like device.

For example, implant 800 may comprise a sack construction that may be filled with a saline or other solution for adjusting the thickness of implant 800. Alternatively another liquid of gel may be used to fill the contents of the sack construction. The liquid or gel should be of a chemical composition that is safe for use in and about the eye, since any damage or malfunctioning of the implant 800 may cause the gel or liquid to ooze out of the implant 800 and come in direct contact with the eye. Implant 800 may also comprise a sack construction that may be filled with air in order to establish the required thickness of section 802. It may also be possible to design implant 800, such that its liquid or gel content gradually seep out of the implant 800 in order to automatically deliver a particular medicated solution to the eye or orbit. In such an exemplary embodiment, the implant 800 may serve both as a medical or drug delivery device, and as a means for repositioning the eyeball. The implant may include a dedicated region (not shown) that is filled with medication for the purpose of delivery to the eye or orbit following the positioning of the implant within the eye (e.g., see FIG. 7). After a finite period of time, it may also be necessary for the doctor or surgeon (e.g., opthalmologist or oculoplastic surgeon) to refill the dedicated region of implant 800 with medication.

After a finite period of time, it may be necessary for the doctor or surgeon (e.g., opthalmologist or oculoplastic surgeon) to refill the contents of the implant 800 in order to reposition the eyeball, where the refill may be medicated or non-medicated. Once refilled, it may also be possible, through a delivery mechanism (e.g., miniature valve, syringe, etc.), to ensure that the implant's 800 contents does not more readily seep out of the implant and into the eye. Once implant 800 is filled with a gel or liquid solution (e.g., by means of a syringe), the opening through which the gel or liquid was delivered may be sealed using, for example, an adhesive material. The opening may also be sealed using a multitude of other techniques. In other embodiment, different valve mechanisms (not shown) may be utilized to control the flow of gel or liquid into and out of implant 800.

For example, implant 800 may comprise a poly(N-isopropylacrylamide) material or other gel-type composition that provides a controllable volume change (e.g., expansion ratio) based on the absorption of a liquid such as, for example, water. For example, by controllably applying the liquid (e.g., water) to the poly(N-isopropylacrylamide) material, thicknesses t1 (FIG. 8A) may be adjusted to thicknesses t2 (FIG. 8B). Such gel-type materials for use in implant 800 may be manufactured by POLY-GEL L.L.C., based in Whippany, N.J. The exemplary embodiments of the implants described herein may be constructed from other materials such as porous polyethylene & polypropylene.

Figure 9A:
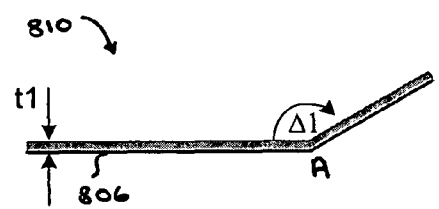
Figure 9B:
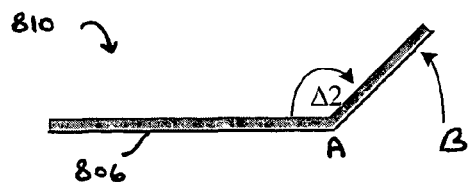

Although implant 800 may be used for controlling the height position of the eyeball (i.e., inferior-superior direction), implant 810 (FIG. 9A) may additionally be adapted to provide a forward positioning of the eyeball (i.e., posterior-anterior direction), as illustrated in the embodiments of FIGS. 9A and 9B. As illustrated in FIG. 9A, implant 810 may comprise a backing or portion 806 that maintains a given shape when manipulated. For example, at point A, implant 800 may be manipulated to include angle $\Delta 1$. As shown in FIG. 9B, by further manipulating implant 810 along the direction of arrow B, the implant 810 may be further manipulated to angle $\Delta 2$, thus enabling an increased forward positioning of the eyeball. Implant 810 may also be adapted to provide both a height adjustment and forward position adjustment for the eyeball by varying the thickness (t) of section 812 and the angular position ($\Delta$) between sections 812 and 814, respectively. Similarly, implant 810 may be adapted to provide either a height adjustment or forward position adjustment for the eyeball by varying the thickness (t) of section 812 or the angular position ($\Delta$) between sections 812 and 814, respectively.

It may therefore be appreciated that according to one or more embodiments of the present invention, either or both the height (i.e., along the inferior-superior direction) and forward (i.e., along the posterior-anterior direction) positioning of the eyeball may be adjusted based on the diagnosis and determination of a trained medical professional (e.g., opthalmologist or oculoplastic surgeon).

According to another embodiment of the present invention, for example, a fracture in the floor 102 (FIG. 1) of the orbit 100 (FIG. 1) caused by a trauma may be medically treated by inserting an implant such as implant device 800 over the fracture region of the orbit floor 102 (FIG. 1), using, for example, an inferior conjunctival incision (FIGS. 6A and 6B). According to this embodiment, the thickness (e.g., t1) of region 802 may be adjusted in order to reposition the eyeball following the reduction of any swelling that may occur after the occurrence of the trauma and placement of the implant device 800. The adjustment of the thickness of region 802 may be carried out prior to and/or following the insertion of implant device 800 within the patient's eye (e.g., under periosteum cover of orbit floor). An embodiment of an implant for both addressing a fracture and the repositioning of the eye is illustrated in FIG. 15.

Figure 10A:
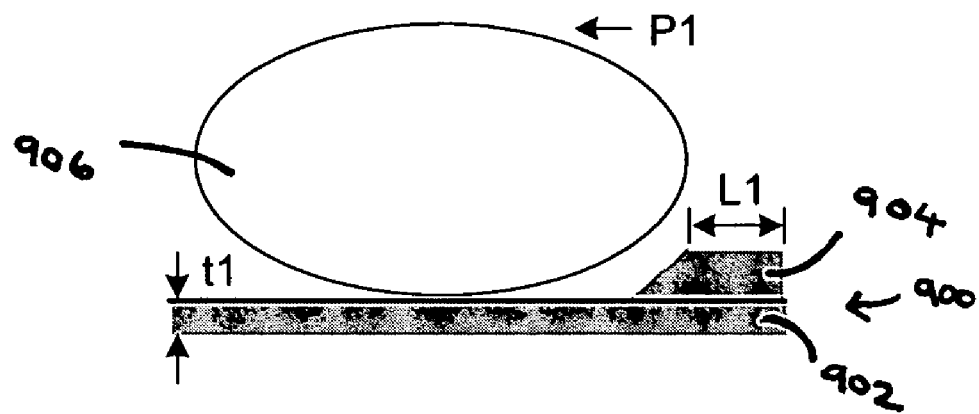
Figure 10B:
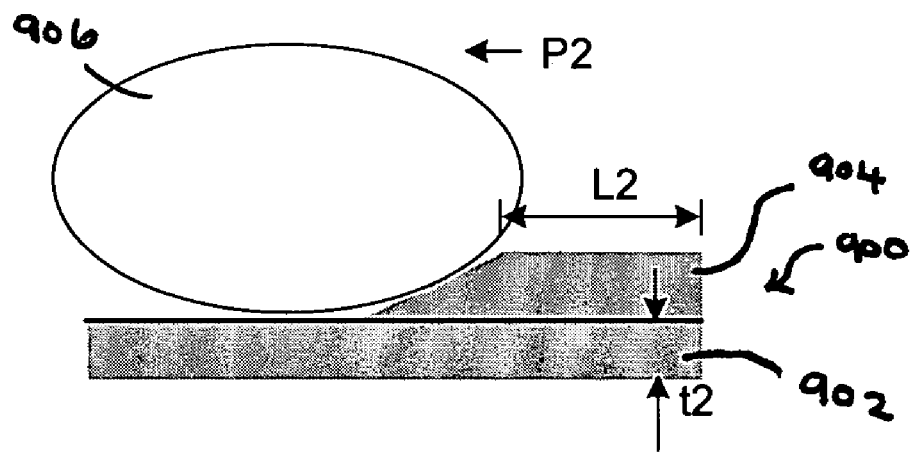

FIGS. 10A and 10B illustrate an implant device 900 according to another embodiment of the present invention. Implant 900 includes a first region 902 and a second region 904, where region 902 may be adapted to adjust the height position of eyeball 906 and region 904 may be adapted to provide forward direction adjustment for eyeball 906. The dimensions of regions 902 and 904 may be independently or simultaneously manipulated in order to relocate the eyeball 906 to a designated position. For example, by controllably varying the thickness of region 902 from t1 to t2 using previously described techniques (e.g., use of gel-type composition), the height position of eyeball 906 may be varied. Also, for example, by controllably varying the length of region 904 from L1 to L2 using previously described techniques (e.g., use of gel-type composition), the forward positioning of eyeball 906 may be varied from position P1 to P2.

It may be appreciated that the dimensions of the implant devices may be manipulated or varied prior to, following, and/or both prior to and following actually being implanted within a patient's eye. This may, among other things, depend on the surgical procedure for placing the implant, the method of controlling the implant dimension (e.g., through a valve, radiation exposure, etc.), the size of the implant device, and the magnitude of repositioning needed based on a patient's condition.

Figure 11A:
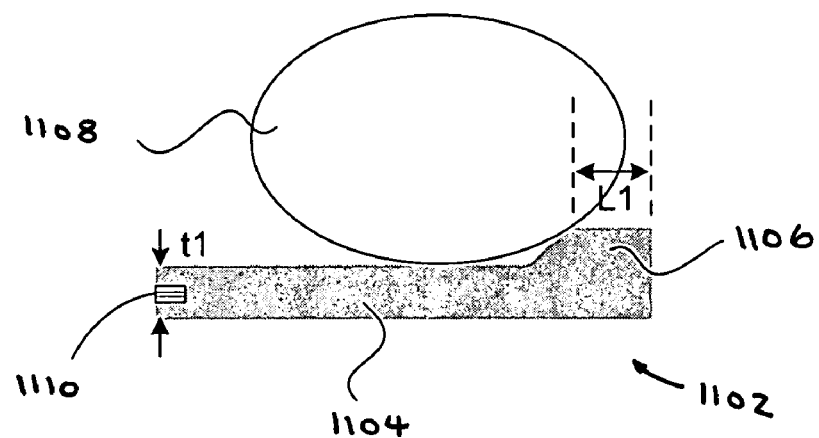
FIGS. 11-12 are cross sectional views of orbital implants according to another embodiment of the present invention.
Figure 11B:
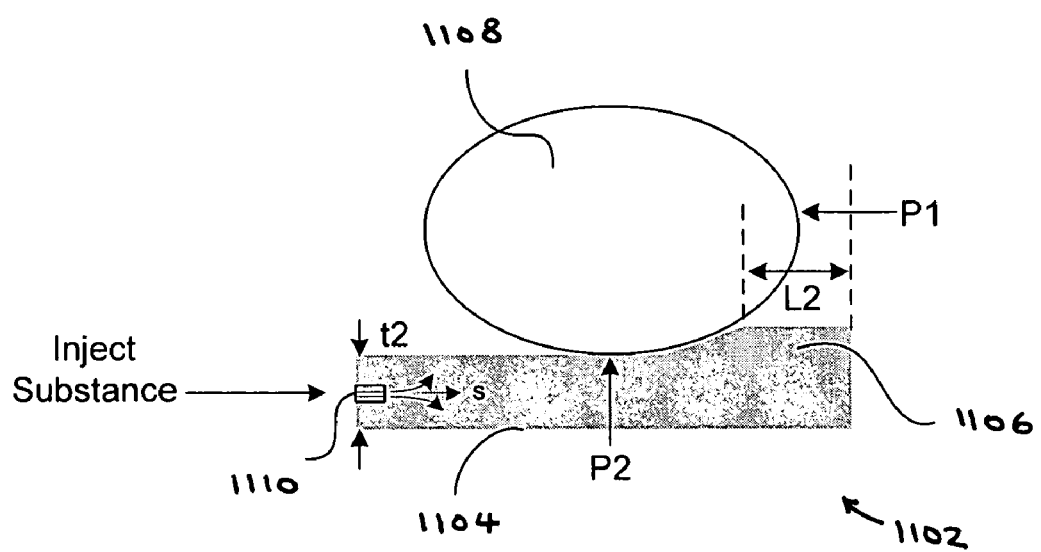

FIGS. 11A and 11B illustrate yet another implant device 1102 according to an embodiment of the present invention. Implant 1102 includes a first region 1104 and a second region 1106, where region 1104 may be adapted to adjust the height position of eyeball 1108 and region 1106 may be adapted to provide forward direction adjustment for eyeball 1108. The dimensions of regions 1104 and 1106 may be manipulated, by intake valve mechanism 1110, in order to reposition the eyeball 1108 to a designated position. For example, the thickness (t1) of region 1104 and the length (L1) of region 1106 may be controllably varied by applying liquid (e.g., saline), gas (e.g., air), or other substances to implant 1102 via valve 1110. Application of a substance to the implant may increase the thickness dimension of region 1104 for t1 to t2 and the length dimension of region 1106 from L1 to L2.

Figure 12A:
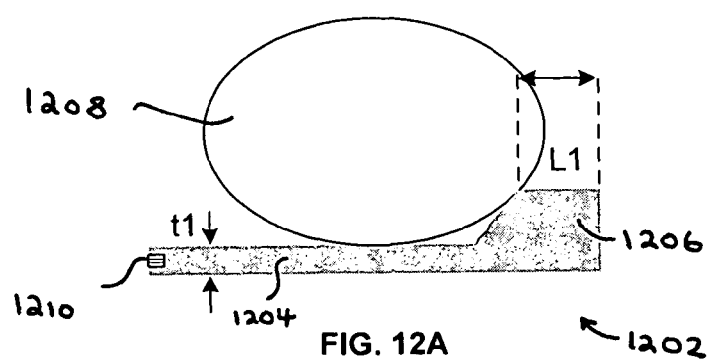
Figure 12B:
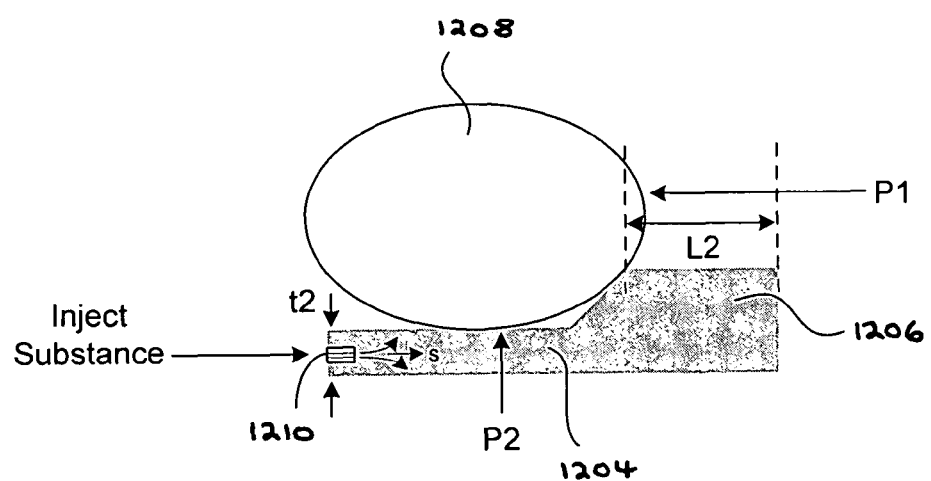

The initial ratio of the thickness (t1) of region 1104 to the length (L1) of region 1106 may be manufactured to different values based on the diagnosed magnitude of forward and upward repositioning of eyeball 1108. For example, as illustrated in FIGS. 11A and 11B, implant 1102 provides more upward repositioning of eyeball 1108 compared to the forward repositioning. This may be evident from the amount by which the thicknesses and length dimension of regions 1104 and 1106 have varied through the injected substance at valve 1110. As illustrated, thickness t1 has increased significantly from t1 to t2 in region 1104, where length L1 has increased by a relatively small amount to length L2 in region 1106. In the embodiment of FIGS. 12A and 12B, implant 1202 provides approximately as much forward repositioning of eyeball 1208 compared to the upward repositioning. This may be evident from the amount by which the thicknesses and length dimension of regions 1204 and 1206 have varied through the injected substance at valve 1210. As illustrated, thickness t1 has significantly increased from t1 to t2 in region 1204, and length L1 has also increased significantly relative to length L2 in region 1206. Thus, implant 1202 may be used when a significant amount of forward and upward repositioning of the eyeball is needed in approximately the same ratio. Alternatively, for example, implant 1102 may be adapted during a diagnosis where more upward repositioning than forward repositioning of the eyeball is needed. Therefore, different implants including various regional dimensions may be manufactured, whereby the ratio between the dimensional changes associated with each regional dimension provides for different ratios of forward and upward eyeball repositioning. Apart from this ratio, controlling the amount of injected substance (e.g., saline) or stimulant (e.g., wavelength radiation) may also provide the necessary dimensional expansion required by a user (e.g., opthalmologist) of an implant device.

Figure 13:
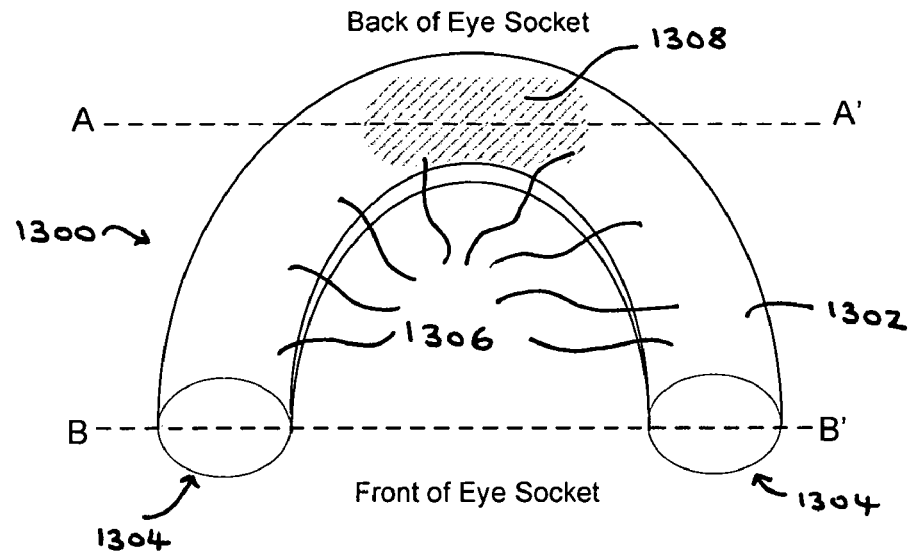
Figure 13:
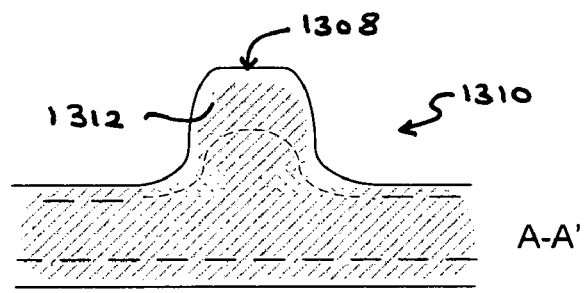
Figure 13:
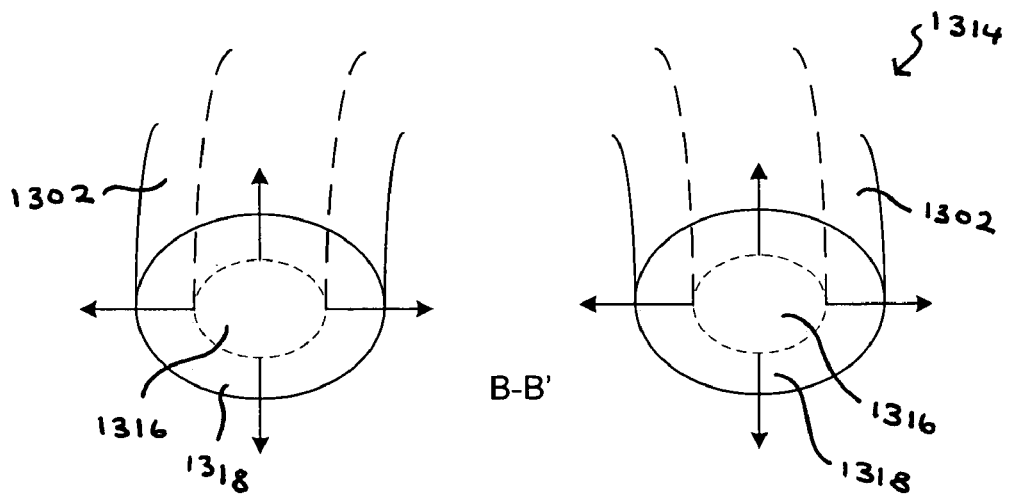

FIG. 13A-FIG. 13C illustrate an implant device 1300 according to another embodiment of the invention. As illustrated, implant 1300 may be implemented substantially in the form of an elongated cylindrical body 1302 of a substantially circular shape (e.g., a semi-circle). For example, the implant may comprise, at least in part, the shape of a donut. In the illustrated example, implant 1300 is shaped in likeness to a half donut or a partially circular elongated cylindrical body 1302. In other embodiments, for example, implant 1300 may be shaped as a whole donut (not shown), a three quarter donut (not shown), or any other portion of a donut-like shape. The cylindrical body 1302 includes a cross section 1304 of a circular shape, but may also include other cross sectional profiles. For example, cross section 1304 may be elliptical, semicircular, triangular, or multisided (hexagonal). If a semicircular cross section is adopted in the construction of implant 1300, the flat base of the semicircle is coupled to the floor or the eye socket, while the eyeball is supported by the semicircular surface. Cylindrical body 1302 may also include region 1308 for providing a forward repositioning of the eyeball. In the exemplary embodiment, a cross section of region 1308 is shown along axis A-A', as indicated at 1310. Region 1308 may include section 1312 for facilitating the forward repositioning of the eyeball, once implant 1300 is subjected to one or more of the previously described techniques (e.g., liquid intake via a valve mechanism) for manipulating its dimensionality. By manipulating the dimensionality of implant 1300, section 1312 may expand in a direction that may be described as perpendicular to and coming out of the surface of the page. The direction and force of this expansion provides the forward repositioning of the eyeball.

As illustrated at 1314, the cross section of body 1302 along axis B-B' is shown. By manipulating the dimensionality of implant 1300, cross section 1316 of body 1302 may increase to cross section 1318. This cross sectional increase or swelling of the implant body 1302 may provide lift or an upward repositioning for the eyeball, where the eyeball is supported by surface 1306 of cylindrical body 1302. Placement and support of the eyeball by surface 1306 of the implant's body distributes the weight and downward force exerted by the eyeball across the implant's surface. This may, among other things, prolong the implant's capability of maintaining its dimensionality upon being utilized for repositioning the eyeball over an extended period of time. Also, the upward force exerted by surface 1306 on the eyeball is not limited to a single point of contact with the eyeball. Accordingly, less pressure is applied by implant 1300 to the eyeball and the various muscles (e.g., inferior rectus muscle) that are coupled to, and control, the eyeball's movement.

Figure 14:
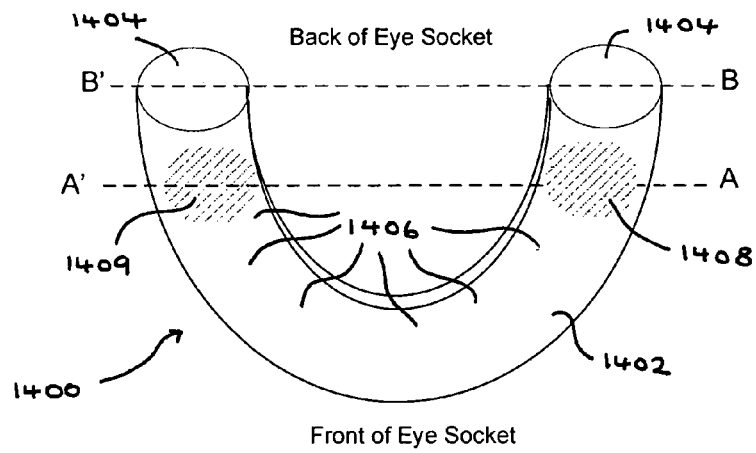
Figure 14:
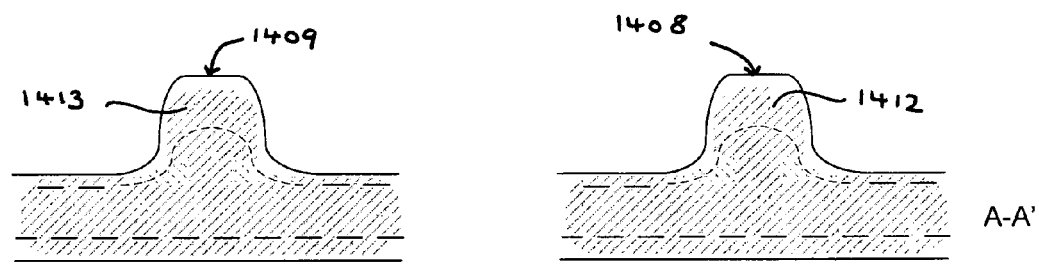
Figure 14:
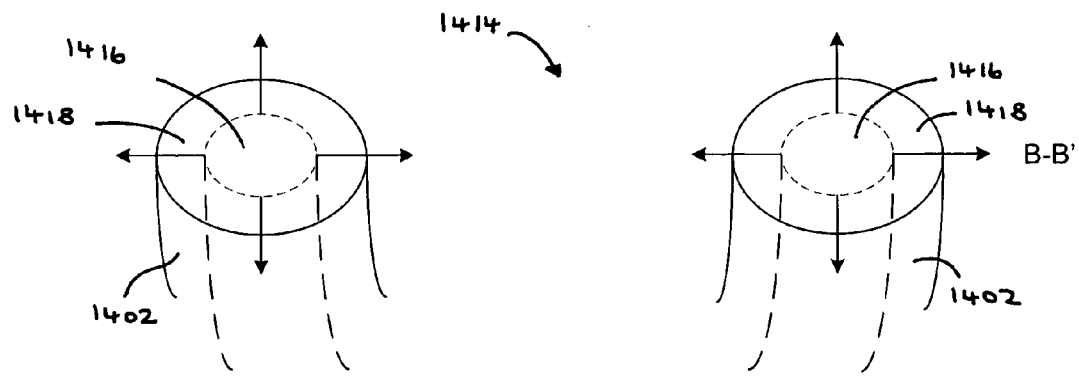

FIG. 14A-FIG. 14C illustrate an implant device 1400 according to yet another embodiment of the invention. As illustrated, implant 1400 may be implemented substantially in the form of an elongated cylindrical body 1402 of a substantially circular shape (e.g., a semi-circle). For example, the implant may comprise, at least in part, the shape of a donut. In the illustrated example, implant 1400 may be shaped in likeness to a half donut or a partially circular elongated cylindrical body 1402. In other embodiments, for example, implant 1400 may be shaped as a whole donut (not shown), a three quarter donut (not shown), or any other portion of a donut-like shape. The cylindrical body 1402 includes a cross section 1404 of a circular shape, but may also include other cross sectional profiles. For example, cross section 1404 may be elliptical, semicircular, triangular, or of a multisided (hexagonal) shape. If a semicircular cross section is adopted in the construction of implant 1400, the flat base of the semicircle may be coupled to the floor or the eye socket, while the eyeball may be supported by the semicircular surface. Cylindrical body 1402 may also include regions 1408 and 1409 for providing a forward repositioning of the eyeball. In the exemplary embodiment, a cross section of regions 1408 and 1409 is shown along axis A-A', as indicated at 1410. Regions 1408 and 1409 each may include sections 1412 and section 1413, respectively, for facilitating the forward repositioning of the eyeball, once implant 1400 is subjected to one or more of the previously described techniques (e.g., liquid intake via a valve mechanism) for manipulating its dimensionality. By manipulating the dimensionality of implant 1400, sections 1412 and 1413 may expand in a direction that may be described as perpendicular to and coming out of the surface or plane of the page. The direction and force of this expansion provides the forward repositioning of the eyeball.

As illustrated at 1414, the cross section of body 1402 along axis B-B' is shown. By manipulating the dimensionality of implant 1400, cross section 1416 of body 1402 may increase to cross section 1418. This cross sectional increase or swelling of the implant body 1402 may provide lift or an upward repositioning for the eyeball, whereby the eyeball is supported by surface 1406 of cylindrical body 1402. Placement and support of the eyeball by surface 1406 of the implant's body distributes the weight and downward force exerted by the eyeball across the implant's surface 1406. This may, among other things, prolong the implant's capability of maintaining its dimensionality upon being utilized for repositioning the eyeball over an extended period of time. Also, the upward force exerted by surface 1406 on the eyeball is not limited to a single point of contact with the eyeball. Accordingly, less pressure is applied by implant 1400 to the eyeball and the various muscles (e.g., inferior rectus muscle) that are coupled to, and control, the eyeball's movement.

While the invention has been described and illustrated in connection with preferred embodiments, many variations and modifications as will be evident to those skilled in this art may be made without departing from the spirit and scope of the invention, and the invention is thus not to be limited to the precise details of methodology or construction set forth above as such variations and modifications are intended to be included within the scope of the invention. Except to the extent necessary or inherent in the processes themselves, no particular order to steps or stages of methods or processes described in this disclosure, including the Figures, is implied. In many cases the order of process steps may be varied without changing the purpose, effect or import of the methods described.

What is claimed is:

1. An orbital implant device adapted to manipulate the position of an eyeball associated with a patient, the device comprising an insertion device, the insertion device including a first and a second portion, the first portion including a first thickness and adapted to elevate the position of the eyeball by controllably manipulating the first thickness and the second portion including a second thickness and adapted to move the position of the eyeball in a forward direction by controllably manipulating the second thickness, wherein the first thickness and the second thickness are configured to be independently controllable.

2. The device according to claim 1, wherein the insertion device comprises an intake mechanism for controlling the first thickness, whereby controlling the first thickness is associated with elevating the position of the eyeball.

3. The device according to claim 2, wherein the intake mechanism comprises a valve device.

4. The device according to claim 1, wherein the insertion device comprises an intake mechanism for controlling second thickness, whereby controlling the second thickness is associated with moving the eyeball in the forward direction.

5. The device according to claim 1, wherein the first portion and second portion comprise an obtuse angle.

6. The device according to claim 5, wherein the obtuse angle comprises a range of about 145-160 degrees.

7. The device according to claim 1, wherein the insertion device comprises a first and a second intake mechanism for controlling the first and second thickness, respectively, whereby controlling the first and second thickness is associated with elevating the position of the eyeball and moving the eyeball in the forward direction, respectively.

8. The device according to claim 1, wherein the insertion device comprises a poly (N-isopropylacrylamide) material, wherein the controlled application of an aqueous fluid to the poly (N-isopropylacrylamide) material of the first portion is associated with manipulating the first thickness.

9. The device according to claim 1, wherein the insertion device comprises a poly(N-isopropylacrylamide) material, wherein the application of an aqueous fluid to the poly(N-isopropylacrylamide) material of the second portion is associated with manipulating the second thickness.

10. The device according to claim 1, wherein the insertion device comprises a poly(N-isopropylacrylamide) material, wherein the application of an aqueous fluid to the poly(N-isopropylacrylamide) material of both the first and the second portion is associated with manipulating the first and the second thickness, respectively.

* * * * *